US 6,521,414 B2
Feb. 18, 2003

(12) United States Patent
Melcher et al.

(54) METHODS FOR IDENTIFYING A MODULATOR OF THE INTERACTION OF NMDA RECEPTOR WITH PROTEIN TYROSINE PHOSPHATASE L1

(75) Inventors: Thorsten Melcher, San Francisco, CA (US); Kalev Kask, San Mateo, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/774,481

(22) Filed: Jan. 30, 2001

(65) Prior Publication Data

US 2001/0049348 A1 Dec. 6, 2001

Related U.S. Application Data

(60) Provisional application No. 60/179,453, filed on Feb. 1, 2000.

(51) Int. Cl.$^7$ ............................. G01N 33/53; C12Q 1/68
(52) U.S. Cl. ............................. 435/7.2; 435/6; 435/7.1; 435/7.92
(58) Field of Search ............................. 435/7.1, 7.92, 435/6, 7.2

(56) References Cited

U.S. PATENT DOCUMENTS 5,821,075 A * 10/1998 Gonez et al. ................. 435/21
5,849,895 A * 12/1998 Daggett et al. ............. 536/23.5

OTHER PUBLICATIONS

Christie, J. M., et al., "Insulin causes a transient tyrosine phosphorylation of NR2A and NR2B NMDA receptor subunits in rat hippocampus", *J. Nerochem.*, 72(4):1523–8, (1999).

Vallano, M. L., "Developmental Aspects of NMDA Receptor Function", *Critical Reviews in Neurobiology*, 12(3):177–204 (1998).

Hironaka, K., et al., "The Protein–tyrosine Phosphatase PTPMEG Interacts with Glutamate Receptor δ2 and ε Subunits", *J. Biol. Chem.*, 275(21):16167–16173 (2000).

Walikonis, R. S., et al., "Identification of Proteins in the Postsynaptic Density Fraction by Mass Spectrometry" *The Journal of Neuroscience*, 20(11):4069–4080 (2000).

Husi, H., et al., "Proteomic analysis of NMDA receptor—adhesion protein signaling complexes", *Nature*, 3(7):661–669 (2000).

Lin, S., et al., "Brain–derived neurotrophic factor enhances association of protein tyrosine phosphatase PTP1D with the NMDA receptor subunit NR2B in the cortical postsynaptic density", *Molecular Brain Research*, 70:18–25 (1999).

Wang, Y. T., et al., "$Ca^{2+}$–independent reduction of N–Methyl–D–aspartate channel activity by protein tyrosine phosphatase", *Proc. Natl. Acad. Sci. USA*, 93:1721–1725 (1996).

Wang, Y. T., et al., "Regulation of NMDA receptors by tyrosine kinases and phosphatases", *Nature*, 369:233–235 (1994).

* cited by examiner

*Primary Examiner*—Elizabeth Kemmerer
*Assistant Examiner*—Ruixiang Li
(74) *Attorney, Agent, or Firm*—Pamela J. Sherwood; Bozicevic, Field & Francis LLP

(57) ABSTRACT

The present invention relates to the identification of a binding between NMDA receptor (NMDA-R) subunits and a protein tyrosine phosphatase (PTP), e.g., PTPL1. The present invention provides methods for screening a PTPL1 agonist or antagonist that modulates NMDA-R signaling. The present invention also provide methods and compositions for treatment of disorders mediated by abnormal NMDA-R signaling. The present invention further provides methods for isolating PTPL1 from a biological preparation.

12 Claims, No Drawings

METHODS FOR IDENTIFYING A MODULATOR OF THE INTERACTION OF NMDA RECEPTOR WITH PROTEIN TYROSINE PHOSPHATASE L1

CROSS-REFERENCE TO RELATED APPLICATIONS

This application claims priority to U.S. provisional patent application No. 60/179,453, filed Feb. 1, 2000, to disclosure of which is incorporated by reference in its entirety.

FIELD OF THE INVENTION

The invention relates in general to the N-methyl-D-aspartate (NMDA) receptor and its signaling activity. The invention provides methods for identifying agonists and antagonists of NMDA receptor signaling, as well as compositions and methods useful for treating physiologic and pathologic conditions mediated by the NMDA receptor. The invention finds application in the biomedical sciences.

BACKGROUND OF THE INVENTION

In the majority of mammalian excitatory synapses, glutamate (Glu) mediates rapid chemical neurotransmission by binding to three distinct types of glutamate receptors on the surfaces of brain neurons. Although cellular responses mediated by glutamate receptors are normally triggered by exactly the same excitatory amino acid (EAA) neurotransmitters in the brain (e.g., glutamate or aspartate), the different subtypes of glutamate receptors have different patterns of distribution in the brain, and mediate different cellular signal transduction events. One major class of glutamate receptors is referred to as N-methyl-D-aspartate receptors (NMDA-Rs), since they bind preferentially to N-methyl-D-aspartate (NMDA). NMDA is a chemical analog of aspartic acid; it normally does not occur in nature, and NMDA is not present in the brain. When molecules of NMDA contact neurons having NMDA-Rs, they strongly activate the NMDA-R (i.e., they act as a powerful receptor agonist), causing the same type of neuronal excitation that glutamate does. It has been known that excessive activation of NMDA-R plays a major role in a number of important central nervous system (CNS) disorders, while hypoactivity of NMDA-R has been implicated in several psychiatric diseases.

NMDA-Rs contain an NR1 subunit and at least one of four different NR2 subunits (designated as NR2A, NR2B, NR2C, and NR2D). NMDA-Rs are "ionotropic" receptors since they control ion channels. These ion channels allow ions to flow into a neuron, thereby activating (depolarizing) the neuron, when the receptor is activated by glutamate, aspartate, or an agonist drug.

Protein tyrosine phosphorylation plays an important role in regulating diverse cellular processes. The regulation of protein tyrosine phosphorylation is mediated by the reciprocal actions of protein tyrosine kinases (PTKs) and protein tyrosine phosphatases (PTPs). NMDA-Rs are regulated by protein tyrosine kinases and phosphatases. Phosphorylation of NMDA-R by protein tyrosine kinases results in enhanced NMDA-R responsiveness in neurons (Wang et al., Nature 369:233–235, 1994). NR2B and NR2A have been shown to be the main sites of phosphorylation by protein tyrosine kinases. Protein tyrosine phosphatases, on the other hand, exert opposing effects on the responsiveness of NMDA-R in the neurons (Wang et al, Proc. Natl. Acad. Sci. U.S.A. U.S.A. 93:1721–1725, 1996). It is believed that members of the Src family of protein tyrosine kinases mediate the NMDA-R tyrosine phosphorylation. On the other hand, the identity of the enzyme responsible for the counter dephosphorylation of NMDA-R has been elusive.

SUMMARY OF THE INVENTION

In one aspect, the present invention provides methods for identifying a modulator of N-methyl-D-aspartate receptor (NMDA-R) signaling by detecting the ability of an agent to modulate the phosphatase activity of a protein tyrosine phosphatase (PTP), e.g., on a NMDA-R substrate, or to modulate the binding of the PTP to NMDA-R. In one embodiment, the modulator is identified by detecting its ability to modulate the phosphatase activity of the PTP. In another embodiment, the modulator is identified by detecting its ability to modulate the binding of the PTP and the NMDA-R.

In a related aspect, the invention provides methods for identifying an agent as a modulator of NMDA-R signaling. The methods contain the steps of (a) contacting the agent with a composition containing PTPL1 and NMDA-R; (b) measuring the tyrosine phosphorylation level of the NMDA-R in the composition; and (c) comparing the NMDA-R tyrosine phosphorylation level thus obtained to the tyrosine phosphorylation level of the NMDA-R in the composition obtained in the absence of the agent. In an aspect, the invention provides a method for identifying an agent as a modulator of NMDA-R signaling, by contacting the (i) agent, (ii) PTPL1 (or a functional derivative thereof), and (iii) NMDA-R, NMDA-R subunit (or a functional derivative thereof), wherein either or both of (ii) and (iii) is substantially pure or recombinantly expressed; measuring the tyrosine phosphorylation level of NMDA-R (or functional derivative thereof) and comparing the tyrosine phosphorylation level in the presence of the agent with the tyrosine phosphorylation level in the absence of the agent, where a difference in tyrosine phosphorylation levels identifies the agent as a modulator of NMDA-R signaling. In one embodiment, the agent is identified by detecting its ability to enhance the PTPL1 dephosphorylation of the NMDA-R. In another embodiment, the agent is identified by detecting its ability to inhibit PTPL1 dephosphorylation of NMDA-R. In some related embodiments, the agent is screened for its ability to modulate binding of the PTPL1 to the NMDA-R. In one embodiment, the agent promotes or enhances the binding. In another embodiment, the agent disrupts or inhibits the binding. In certain other embodiments, the NMDA-R and the PTPL1 are present in a PTPL1/NMDA-R-containing protein complex.

In another related aspect, methods for identifying a nucleic acid molecule that modulates NMDA-R signaling are provided. Such methods contain the steps of introducing a nucleic acid molecule encoding a gene product into cells co-expressing the NMDA-R and PTPL1; culturing the cells harboring the nucleic acid molecule under conditions in which the gene product is expressed; measuring the tyrosine phosphorylation level of the NMDA-R in the cells containing the gene product; and comparing the NMDA-R tyrosine phosphorylation level thus obtained to NMDA-R tyrosine phosphorylation level in cells that do not harbor the nucleic acid molecule. Thus, the invention provides a method for identifying a nucleic acid molecule that modulates NMDA-R signaling, by (a) obtaining a cell culture coexpressing the NMDA-R (or functional derivative thereof) and PTPL1 (or functional derivative thereof), (b) introducing a nucleic acid molecule encoding a gene product into a portion of the cells; thereby producing cells comprising the nucleic acid molecule; (c) culturing the cells in (b) under conditions in which the gene product is expressed; (d) measuring the tyrosine phosphorylation level of the NMDA-R in the cells in (c) and comparing the level with that of control cells into which the nucleic acid molecule has not been introduced, wherein a difference in tyrosine phosphorylation levels identifies the nucleic acid molecule as a modulator of NMDA-R signaling.

In another aspect, the invention provides methods for treating a disease mediated by abnormal NMDA-R-signaling by administering a modulator of a PTPL1 activity that modulate the tyrosine phosphorylation level of the NMDA-R. In some embodiments, the modulator modulates the ability of PTPL1 to dephosphorylate NMDA-R. In some related embodiments, the modulator modulates the ability of PTPL1 to bind to NMDA-R. In certain embodiments, the modulator is a PTPL1 agonist and the disease to be treated is mediated by excessive NMDA-R signaling. In some other embodiments, the modulator is a PTPL1 antagonist and the disease to be treated is mediated by NMDA-R hypofunction.

In another aspect, the invention provides a method for isolating a polypeptide containing the PDZ2 domain of PTPL1 from a biological preparation containing the polypeptide.

In another aspect, the invention provides the use of an agent that modulates PTPL1 phosphatase activity in the treatment of a disease or condition mediated by NMDA-receptor activity or signaling.

In another aspect, the invention provides the use of a modulator (e.g. agonist or antagonist) of PTPL1 phosphatase activity in the manufacture of a medicament for treatment of a disease or condition mediated by NMDA-receptor activity or signaling.

DETAILED DESCRIPTION

The present invention relates to the discovery of a binding interaction between the NR2A or NR2B subunits of the NMDA-R and a protein tyrosine phosphatase, PTPL1. In accordance with the discovery, the present invention provides methods for identifying agonists and antagonists of PTPL1 that modulate NMDA-R signaling, and for treating conditions mediated by abnormal NMDA-R signaling. The following sections provide guidance for making and using the compositions of the invention, and for carrying out the methods of the invention.

I. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, the preferred methods and materials are described. The following definitions are provided to assist the reader in the practice of the invention.

As used herein, the term "acute insult to the central nervous system" includes short-term events which pose a substantial threat of neuronal damage mediated by glutamate excitotoxicity. These include ischemic events (which involve inadequate blood flow, such as a stroke or cardiac arrest), hypoxic events (involving inadequate oxygen supply, such as drowning, suffocation, or carbon monoxide poisoning), trauma to the brain or spinal cord (in the form of mechanical or similar injury), certain types of food poisoning which involve an excitotoxic poison such as domoic acid, and seizure-mediated neuronal degeneration, which includes certain types of severe epileptic seizures. It can also include trauma that occurs to another part of the body, if that trauma leads to sufficient blood loss to jeopardize blood flow to the brain (for example, as might occur following a shooting, stabbing, or automobile accident).

The term "agent" includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

As used herein, an "agonist" is a molecule which, when interacting with (e.g., binding to) a reference protein (e.g., PTPL1, NMDA-R), increases or prolongs the amount or duration of the effect of the biological activity of the reference protein. By contrast, the term "antagonist," as used herein, refers to a molecule which, when interacting with (e.g., binding to) a reference protein, decreases the amount or the duration of the effect of the biological activity of the reference protein (e.g., PTPL1 or NMDA-R). Agonists and antagonists may include proteins, nucleic acids, carbohydrates, antibodies, or any other molecules which decrease the effect of a reference protein. Unless otherwise specified, the term "agonist" can be used interchangeably with "activator", and the term "antagonist" can be used interchangeably with "inhibitor".

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

The term "biological preparation" refers to biological samples taken in vivo and in vitro (either with or without subsequent manipulation), as well as those prepared synthetically. Representative examples of biological preparations include cells, tissues, solutions and bodily fluids, a lysate of natural or recombinant cells.

As used herein, the term "functional derivative" of a native protein or a polypeptide is used to define biologically active amino acid sequence variants that possess the biological activities (either functional or structural) that are substantially similar to those of the reference protein or polypeptide. Thus, a functional derivative of PTPL1 must retain, among other activities, the ability to bind and dephosphorylate the NMDA-R. Similarly, a functional derivative of NMDA-R must be capable of binding to PTPL1, and being phosphorylated by PTPL1.

As used herein, the term "modulator of NMDA-R signaling" refers to an agent that is able to alter an NMDA-R activity that is involved in the NMDA-R signaling pathways. The modulators include, but are not limited to, both "activators" and "inhibitors" of NMDA-R tyrosine phosphorylation. An "activator" is a substance that enhances the tyrosine phosphorylation level of NMDA-R, and thereby causes the NMDA receptor to become more active. The mode of action of the activator may be direct, e.g., through binding the receptor, or indirect, e.g., through binding another molecule which otherwise interacts with NMDA-R (e.g., PTPL1). Conversely, an "inhibitor" decreases the tyrosine phosphorylation of NMDA-R, and thereby causes NMDA receptor to become less active. The reduction may be complete or partial. As used herein, modulators of NMDA-R signaling would encompass PTPL1 antagonists and agonists.

The term "modulation" as used herein refers to both upregulation, (i.e., activation or stimulation), for example by agonizing; and downregulation (i.e. inhibition or suppression), for example by antagonizing, of a bioactivity (e.g., NMDA-R tyrosine phosphorylation, PTPL1 tyrosine phosphatase activity, PTPL1 binding to NMDA-R).

The term "NMDA-R hypofunction" is used herein to refer to abnormally low levels of signaling activity of NMDA-Rs on CNS neurons. For example, NMDA-R hypofunction may be caused by, e.g., abnormally low phosphotyrosine level of NMDA-R. NMDA-R hypofunction can occur as a drug-induced phenomenon. It can also occur as an endogenous disease process.

Unless otherwise specified, the term "NMDA-R" or "NMDA receptor" as used herein refers to an NMDA receptor molecule that has an NR1 subunit and at least one NR2A or NR2B subunit.

As used herein, the term "NMDA-R signaling" refers to its signal-transducing activities in the central nervous system that are involved in the various cellular processes such as neurodevelopment, neuroplasticity, and excitotoxicity. NMDA-R signaling affects a variety of processes including, but not limited to, neuron migration, neuron survival, synaptic maturation, learning and memory, and neurodegeneration.

As used herein, the term "PTPL1 modulator" includes both "activators" and "inhibitors" of PTPL1 phosphatase activity on NMDA-R. An "activator" of PTPL1 is a substance which causes PTPL1 to become more active, and thereby decrease the phosphotyrosine level of NMDA-R. The mode of action of the activator may be direct, e.g., through binding PTPL1, or indirect, e.g., through binding another molecule which otherwise interacts with PTPL1. Conversely, an "inhibitor" of PTPL1 is a substance which causes PTPL1 to become less active, and thereby increase phosphotyrosine level of NMDA-R to a detectable degree. The reduction may be complete or partial, and due to a direct or an indirect effect.

As used herein, the term "polypeptide containing the PDZ2 domain of PTPL1" includes PTPL1, and other polypeptides that contain the PDZ2 domain of PTPL1, or their derivatives, analogs, variants, or fusion proteins that can bind to NR2A and/or NR2B. The term "polypeptide containing PTPL1-binding site of NMDA-R" include an NMDA-R that has at least an NR2A or NR2B subunit, NR2A, NR2B, and other polypeptides that contain the PTPL1-binding site of NR2A or NR2B, or their derivatives, analogs, variants, or fusion proteins that can bind to PTPL1.

As used herein, the term "PTPL1/NMDA-R-containing protein complex" refers to protein complexes, formed in vitro or in vivo, that contain PTPL1 and NMDA-R. When only the binding of PTPL1 and NMDA-R is of concern, a polypeptide containing the PDZ2 domain of PTPL1 and a polypeptide containing PTPL1-binding site of NMDA-R can substitute for PTPL1 and NMDA-R respectively. However, when dephosphorylation of NMDA-R by PTPL1 is in concern, only a PTPL1 functional derivative and an NMDA-R functional derivative can respectively substitute for PTPL1 and NMDA-R in the complex. In addition, the complex may also comprise other components, e.g., a protein tyrosine kinase.

The terms "substantially pure" or "isolated," when referring to proteins and polypeptides, e.g., a fragment of PTPL1, denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition.

A "variant" of a molecule such as PTPL1 or NMDA-R is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

As used herein, "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid," as used herein, is one that originates from a source foreign to the particular host cell, or, if from the same source, is modified from its original form. Thus, a heterologous gene in a prokaryotic host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, sitespecific mutation, and related techniques.

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding PTPL1) and a promoter. Additional factors necessary or helpful in effecting expression can also be used as described herein. For example, transcription termination signals, enhancers, and other nucleic acid sequences that influence gene expression, can also be included in an expression cassette.

As used herein, "contacting" has its normal meaning and refers to combining two or more agents (e.g., two proteins, a polynucleotide and a cell, etc.). Contacting can occur in vitro (e.g., two or more agents [e.g., a test compound and a cell lysate] are combined in a test tube or other container) or in situ (e.g., two polypeptides can be contacted in a cell by coexpression in the cell, of recombinant polynucleotides encoding the two polypeptides), in a cell lysate"

Various biochemical and molecular biology methods referred to herein are well known in the art, and are described in, for example, Sambrook et al., Molecular Cloning: A Laboratory Manual, Cold Spring Harbor Press, N.Y. Second (1989) and Third (2000) Editions, and Current Protocols in Molecular Biology, (Ausubel, F. M. et al., eds.) John Wiley & Sons, Inc., New York (1987–1999).

II. Identification of Interaction of NMDA-R Subunits with PTPL1 by Yeast Two Hybrid Screening The intracellular protein-tyrosine phosphatase PTPL1 has been cloned and sequenced (see, e.g., U.S. Pat. No. 5,821,075). It has five PDZ domains. PDZ is a conserved protein domain that has been identified in various membrane-associated signaling proteins. For a review of PDZ domain-containing proteins, see Ponting, C. P. et al., Bioessays 19:469–479, 1997. The NMDA-R has also been cloned and characterized (Hollmann et al., Ann. Rev. Neurosci. 17:31–108, 1994; McBain et al., Physiol. Rev. 74:723–760, 1994). Amino acid and nucleic acid sequences for PTPL1, other phosphatases, and NMDA receptor subunits can readily be found public databases (e.g., GenBank) and the scientific literature. For example, exemplary sequences for human clones have the following Genbank accession numbers: PTPL1: X80289; NR2A: NM_000833; NR2B: NM_000834; NR2C: NM_000835; NR2D: NT_011190; NR1: NM_000832. Exemplary sequences for rat clones have the following Genbank accession numbers: NR2A: M91561; NR2B: M91562; NR2C: M91563; NR2D: D13213; NR1: X63255. Additional sequence information is readily available. Further, polynucleotides encoding proteins of interest can be obtained using sequence information by routine methods (e.g., cloning or amplification using probes or primers designed from the sequences). These clones, their homologs and derivatives can be used in the present invention.

As detailed in the Examples, infra, an interaction between the PDZ2 domain of PTPL1 and NR2A or NR2B was identified according to the present invention using a yeast two-hybrid screening system. This interaction is further demonstrated by other approaches including "pull-down" using GST-fusions (Harris, Methods Mol. Biol. 88:87–99, 1998) and co-immunoprecipitation of PTPL1 and an NMDA-R subunit (see the Examples). The physiological significance of this interaction is examined by phosphorylation experiments, electrophysiology, and co-localization approaches. Results from these studies indicate that, unexpectedly, PTPL1 is involved in the dephosphorylation of the NR2B and NR2A subunits of NMDA-R.

III. Screening for Modulators of NMDA-R Signaling

The present invention provides methods for identifying modulators of NMDA-R signaling. The NMDA-R modulators are identified by detecting the ability of an agent to modulate an activity of a protein tyrosine phosphatase (PTP) which is capable of dephosphorylating an NMDA-R. The modulated activities of the PTP include, but are not limited to, its phosphatase activity or its binding to NMDA-R.

Preferably, the PTP used for screening NMDA-R modulators is PTPL1. In one embodiment, the NMDA-R modulators are screened for their ability to modulate PTPL1 phosphatase activity. In another embodiment, the NMDA-R modulators are identified by detecting their ability to promote or suppress the binding of PTPL1 and NMDA-R.

A. Identification of NMDA-R Modulators by Monitoring Dephosphorylation of NMDA-R by PTPL1

In one aspect, NMDA-R modulators of the present invention are identified by monitoring their ability to modulate PTPL1 phosphatase activity. As will be detailed below, PTPL1, the NMDA-R/PTPL1-containing protein complex, or cell lines that express PTPL1 or NMDA-R/PTPL1-containing protein complex, are used to screen for PTPL1 agonists and antagonists that modulate NMDA-R tyrosine dephosphorylation. An agent that enhances the ability of PTPL1 to dephosphorylate NMDA-R will result in a net decrease in the amount of phosphotyrosine, whereas an agent that inhibits the ability of PTPL1 to dephosphorylate NMDA-R will result in a net increase in the amount of phosphotyrosine.

1. In Vitro Assay

In some embodiments, the ability of an agent to enhance or inhibit PTPL1 phosphatase activity is assayed in an in vitro system. In general, the in vitro assay format involves adding an agent to PTPL1 (or a functional derivative of PTPL1) and a substrate of PTPL1, and measuring the tyrosine phosphorylation level of the substrate. In an embodiment, as a control, tyrosine phosphorylation level of the substrate is also measured under the same conditions except that the test agent is not present. By comparing the tyrosine phosphorylation levels of the substrate, PTPL1 antagonists or agonists can be identified. Specifically, a PTPL1 antagonist is identified if the presence of the test agent results in an increased tyrosine phosphorylation level of the substrate. Conversely, a decreased tyrosine phosphorylation level in the substrate indicates that the test agent is a PTPL1 agonist. The invention provides the use of such agents to modulate NMDA-R activity.

PTPL1 used in the assays is obtained from various sources. In some embodiments, PTPL1 used in the assays is purified from cellular or tissue sources, e.g., by immunoprecipitation with specific antibodies. In other embodiments, as described below, PTPL1 is purified by affinity chromatography utilizing specific interactions of PTPL1 with known protein motifs, e.g., the interaction of the PDZ2 domain of PTPL1 with NR2A and/or NR2B. In still other embodiments, PTPL1, either holoenzyme or enzymatically active parts of it, is produced recombinantly either in bacteria or in eukaryotic expression systems. The recombinantly produced variants of PTPL1 can contain short protein tags, such as immunotags (HA-tag, c-myc tag, FLAG-tag) or 6×His-tag, which could be used to facilitate the purification of recombinantly produced PTPL1 using immunoaffinity or metal-chelation-chromatography, respectively.

Various substrates are used in the assays. Preferably, the substitute is NMDA-R, a functional derivative of NMDA-R, or the NR2A or NR2B subunit. In some embodiments, the substrates used are proteins purified from a tissue (such as immunoprecipitated NR2A or NR2B from rat brain). In other embodiments, the substrates are recombinantly expressed proteins. Examples of recombinant substrates include, but are not limited to, NR2A and/or NR2B fusion proteins expressed in *E. coli*, yeast, or mammalian expression systems. In still other embodiments, the substrates used are synthetic peptides that are tyrosine phosphorylated by specific kinase activity, e.g., Src or Fyn kinases.

Methods and conditions for expression of recombinant proteins are well known in the art. See, e.g., Sambrook, supra, and Ausubel, supra. Typically, polynucleotides encoding the phosphatase and/or substrate used in the invention are expressed using expression vectors. Expression vectors typically include transcriptional and/or translational control signals (e.g., the promoter, ribosome-binding site, and ATG initiation codon). In addition, the efficiency of expression can be enhanced by the inclusion of enhancers appropriate to the cell system in use. For example, the SV40 enhancer or CMV enhancer can be used to increase expression in mammalian host cells. Typically, DNA encoding a polypeptide of the invention is inserted into DNA constructs capable of introduction into and expression in an in vitro host cell, such as a bacterial (e.g., *E. coli, Bacillus subtilus*), yeast (e.g., Saccharomyces), insect (e.g., *Spodoptera frugiperda*), or mammalian cell culture systems. Mammalian cell systems are preferred for may applications. Examples of mammalian cell culture systems useful for expression and production of the polypeptides of the present invention include human embryonic kidney line (293; Graham et al., 1977, J. Gen. Virol. 36:59); CHO (ATCC CCL 61 and CRL 9618); human cervical carcinoma cells (HeLa, ATCC CCL 2); and others known in the art. The use of mammalian tissue cell culture to express polypeptides is discussed generally in Winnacker, *From Genes to Clones* (VCH Publishers, N.Y., N.Y., 1987) and Ausubel, supra. In some embodiments, promoters from mammalian genes or from mammalian viruses are used, e.g., for expression in mammalian cell lines. Suitable promoters can be constitutive, cell type-specific, stage-specific, and/or modulatable or regulatable (e.g., by hormones such as glucocorticoids). Useful promoters include, but are not limited to, the metallothionein promoter, the constitutive adenovirus major late promoter, the dexamethasone-inducible MMTV promoter, the SV40 promoter, and promoter-enhancer combinations known in the art.

The substrate may or may not be already in a tyrosine phosphorylated state (Lau & Huganir, J. Biol. Chem., 270: 20036–20041, 1995). In the case of a nonphosphorylated starting material, the substrate is typically phosphorylated, e.g., using an exogenous tyrosine kinase activity such as Src or Fyn.

A variety of standard procedures well known to those of skill in the art are used to measure the tyrosine phosphorylation levels of the substrates. In some embodiments, a phosphotyrosine-recognizing antibody-based assay is used, e.g., radioimmunoassay (RIA), enzyme-linked immunosorbent assay (ELISA), as well as fluorescently labeled antibodies whose binding can be assessed from levels of emitted fluorescence. See, e.g., U.S. Pat. No. 5,883,110; Mendoza et al., Biotechniques. 27: 778–788, 1999. In other embodiments, instead of immunoassays, the substrates are directly labeled with a radioactive phosphate group using kinases that carry out selective tyrosine phosphorylation (Braunwaler et al., Anal. Biochem. 234:23–26, 1996). The rate of removal of radioactive label from the labeled substrate can be quantitated in liquid (e.g., by chromatographic separation) or in solid phase (in gel or in Western blots).

Comparing a tyrosine phosphorylation level under two different conditions (e.g., in the presence and absence of a test agent) sometimes includes the step of recording the level of phosphorylation in a first sample or condition and comparing the recorded level with that of (or recorded for) a second portion or condition.

In some embodiments of the invention, other than adding PTPL1 to a substrate (e.g., NR2A or NR2B), the in vitro assay are performed with an NMDA-R/PTPL1-containing protein complex. Such protein complexes contain NMDA-R and PTPL1, or their functional derivatives. In addition, the complexes may also contain PTK and other molecules. The NMDA-R/PTPL1-containing protein complexes may be obtained from neuronal cells using methods well known in the art, e.g., immunoprecipitation as described in Grant et al. (WO 97/46877). Tyrosine phosphorylation levels of the substrates are assayed with standard SDS-PAGE and immunoblot analysis.

2. In Vivo Assays

In other embodiments, NMDA-R signaling modulators of the present invention are identified using in vivo assays. Such in vivo assay formats usually entail culturing cells co-expressing PTPL1 and its substrate (e.g., NR2A or NR2B; e.g., recombinant forms of PTPL1 and/or NMDA-R subunit substrate(s)), adding an agent to the cell culture, and measuring tyrosine phosphorylation level of the substrate in the cells. In one embodiment, as a control, tyrosine phosphorylation level of the substrate in cells not exposed to the test agent is also measured or determined. In one embodiment, the in vivo screening system is modified from the method described in U.S. Pat. No. 5,958,719. Using this screening system, intact cells that express PTPL1 and a substrate of PTPL1 (e.g., NMDA-R, NR2A, or NR2B) are first treated (e.g., by NMDA) to stimulate the substrate phosphorylation. The cells are then incubated with a substance which can penetrate into the intact cells and selectively inhibit further phosphorylation (e.g., by a PTK) of the substrate (e.g., NMDA-R). The degree of phosphorylation of the substrate is then determined by, e.g., disrupting the cells and measuring phosphotyrosine level of the substrate according to methods described above (e.g., with standard SDS-PAGE and immunoblot analysis). The activity of PTPL1 is determined from the measured degree of phosphorylation of the substrate. An additional measurement is carried out in the presence of an agent. By comparing the degrees of phosphorylation, agonists or antagonist of PTPL1 that modulate NMDA-R tyrosine phosphorylation are identified.

In another embodiment, the present invention provides a method for identifying a nucleic acid molecule encoding a gene product which is capable of modulating the tyrosine phosphorylation level of NMDA-R. In one embodiment, a test nucleic acid is introduced into host cells coexpressing PTPL1 and NMDA-R or their functional derivatives. Methods for introducing a recombinant or exogenous nucleic acid into a cell are well known and include, without limitation, transfection, electroporation, injection of naked nucleic acid, viral infection, liposome-mediated transport (see, e.g., Dzau et al., 1993, Trends in Biotechnology 11:205–210; Sambrook, supra, Ausubel, supra). The cells are cultured so that the gene product encoded by the nucleic acid molecule is expressed in the host cells and interacts with PTPL1 and NMDA-R or their functional derivatives, followed by measuring the phosphotyrosine level of the NMDA-R. The effect of the nucleic acid on NMDA-R-signaling is determined by comparing NMDA-R phosphotyrosine levels measured in the absence or presence of the nucleic acid molecule.

B. Screening for NMDA-R Modulators by Monitoring Binding of PTPL1 and NMDA-R

It will be appreciated by one of skill in the art that modulation of binding of PTPL1 and NMDA-R may also affect the level of tyrosine phosphorylation in NMDA-R by PTPL1. Therefore, agents identified from screening using the in vivo and in vitro assay systems described above may also encompass agents which modulate NMDA-R tyrosine phosphorylation by modulating the binding of PTPL1 and NMDA-R. In some embodiments of the invention, NMDA-R modulators are identified by directly screening for agents that promote or suppress the binding of PTPL1 and NMDA-R. Agents thus identified may be further examined for their ability to modulate NMDA-R tyrosine phosphorylation, using methods described above or standard assays well known in the art.

1. Assays Based on Two-hybrid Screening System

A variety of binding assays are useful for identifying agents that modify the interaction between the PDZ2 domain of PTPL1 and NR2A (or NR2B). In certain embodiments, two-hybrid based assays are used.

i) Yeast Two-hybrid Assay

The cDNAs encoding the C-terminal portion, typically at least 100, 200, 400, or 600 C-terminal amino acid residues, of NR2A or NR2B and at least the PDZ2 domain of PTPL1 are cloned into yeast two-hybrid vectors encoding the DNA binding domain and DNA activation domain, respectively, or vice-versa. The yeast two-hybrid used is based on the yeast GAL4 transcriptional system (Song & Fields, Nature 340: 245–246, 1989), the Sos-Ras complementation system (Aronheim et al., Mol. Cell. Biol. 17: 3094–3102, 1997), the bacterial LexA transcriptional system (*Current Protocols in Mol. Biol.*, Ausubel et al. Eds, 1996, New York), or any other system of at least equal performance. Reporter gene constructs, such as α- or β-galactosidase, β-lactamase, or green fluorescent protein (GFP, see, Tombolini et al., Methods Mol Biol. 102: 285–98, 1998; Kain et al., Methods Mol Biol. 63: 305–24, 1997), are produced using necessary regulatory elements from promoter regions of above-mentioned transcription factors. Alternatively, modular signaling molecules are engineered to be brought together by the interaction between NR2A and/or NR2B and PTPL1 in the Sos-Ras complementation-based yeast two-hybrid system. These constructs are transiently or stably transformed into a yeast strain to be used in the screen.

In one embodiment, the GAL4 system is used to screen agents that modulate the binding of PTPL1 and NMDA-R. DNA binding domain vector containing the C-terminal portion of NR2A or NR2B and DNA activation domain vector containing the PDZ2 domain of PTPL1 are cotransformed into the same yeast strain which carries one of the reporters. The interaction between PTPL1 and NMDA-R activates the expression of the reporter gene. The yeast culture in which the reporter genes is expressed is divided in equal amounts to 96- or 384-well assay plates. The levels of α- or β-galactosidase, β-lactamase are measured by quantifying their enzymatic activity using colorimetric substrates, such as orthomethylphenylthiogalactoside (OMTP) or X-gal; the levels of GFP are assessed fluorometrically. Pools of agents or individual agents are added to yeast cultures in wells and the levels of inhibition or facilitation of the interaction by the agents are determined from the levels of the reporter gene activity. Agents which decrease the reporter gene expression are antagonists of the interaction between PTPL1 and NR2A or NR2B. In contrast, agents which facilitate the reporter gene expression are agonists of the interaction between PTPL1 and NR2A or NR2B.

ii) Bacterial Two-hybrid

The bacterial two-hybrid screening system is based on the reconstitution, in an *Escherichia coli* cya strain, of a signal transduction pathway that takes advantage of the positive control exerted by cAMP (Karimova et al., Proc. Natl. Acad. Sci. U S A. 95:5752–56, 1998). Association of the two-hybrid proteins, such as that of PTPL1 with NR2A and/or NR2B, results in functional complementation between T25 and T18 fragments and leads to cAMP synthesis. Cyclic AMP then triggers transcriptional activation of catabolic operons, such as lactose or maltose, that yield a characteristic phenotype.

iii) Mammalian Two-hybrid

The mammalian two-hybrid assay is also based on transcriptional activation. See, *The Yeast Two-Hybrid System*. Bartel & Fields, Eds. 1997, Oxford, Oxford University Press. In the present invention, the cDNAs encoding at least the C-terminal portion of NR2A or NR2B and at least the PDZ2 domain of PTPL1 are cloned into mammalian two-hybrid vectors encoding the DNA binding domain and the VP16 DNA activation domain, respectively, or vice-versa. These vector constructs are cotransfected into the cell line which harbors a reporter gene (CAT, luciferase, GFP, α- or β-galactosidase, β-lactamase) under the control of the VP16 responsive promoter. Transcriptional activation in cells reflected by the levels of the reporter gene or its activity is proportional to the strength of interaction between the C-terminal portions of NR2A or NR2B and the PDZ2 domain of PTPL1. The cell culture in which the reporter gene is expressed is divided in equal amounts to 96- or 384-well assay plates. The expression levels of CAT, α- or β-galactosidase, β-lactamase are measured by quantifying their enzymatic activity using colorimetric substrates, such as X-gal; the levels of GFP or luciferase are assessed fluorometrically or spectrophotometrically, respectively. Agents which modulate the PTPL1 binding to NR2A and/or NR2B are similarly identified as that described in the yeast two-hybrid assay.

2. Other Binding Assays

In some embodiments of the invention, agents (e.g., peptides) that bind to the PDZ2 domain of PTPL1 with high affinity are identified by phage display, an oriented peptide library approach (Songyang et al., Science 275: 73–77, 1997) or a lacd repressor system (Stricker et al., Methods in Enzymology 303: 451–468, 1999). These peptides are further screened for their ability to modulate the interaction between PTPL1 and NR2A or NR2B.

In one embodiment, modulators of the interaction between PTPL1 and NR2A or NR2B are identified by detecting their abilities to either inhibit PTPL1 and NMDA-R from binding (physically contacting) each other or disrupts a binding of PTPL1 and NMDA-R that has already been formed. The inhibition or disruption can be either complete or partial. In another embodiment, the modulators are screened for their activities to either promote PTPL1 and NMDA-R binding to each other, or enhance the stability of a binding interaction between PTPL1 and NMDA-R that has already been formed. In either case, some of the in vitro and in vivo assay systems discussed above for identifying agents which modulate the NMDA-R tyrosine phosphorylation level may be directly applied or readily modified to monitor the effect of an agent on the binding of NMDA-R and PTPL1. For example, a cell transfected to coexpress PTPL1 and NMDA-R or receptor subunit, in which the two proteins interact to form an NMDA-R/PTPL1-containing complex, is incubated with an agent suspected of being able to inhibit this interaction, and the effect on the interaction measured. In some embodiments, a polypeptide containing the PDZ2 domain of PTPL1 and a polypeptide containing PTPL1-binding site of NMDA-R can substitute for the intact PTPL1 and NMDA-R proteins, respectively, in the NMDA-R/PTPL1-containing protein complexes. Any of a number of means, such as coimmunoprecipitation, is used to measure the interaction and its disruption.

C. Screening for NMDA-R Modulators Using PTPL1 and NMDA-R Functional Derivatives or Subunits Although the foregoing assays or methods are described with reference to PTPL1 and NMDA-R, the ordinarily skilled artisan will appreciate that functional derivatives or subunits of PTPL1 and NMDA-R may also be used. For example, in various embodiments, NR2A or NR2B is used to substitute for an intact NMDA-R in assays for screening agents that modulate binding of PTPL1 and NMDA-R. In a related embodiment, an NMDA-R functional derivative is used for screening agents which modulate PTPL1 phosphatase activity on NMDA-R. In an other embodiment, a polypeptide containing the PDZ2 domain of PTPL1 is used for screening agents which modulate the binding of PTPL1 and NMDA-R.

Further, in various embodiments, functional derivatives of PTPL1 that have amino acid deletions and/or insertions and/or substitutions (e.g., conservative substitutions) while maintaining their catalytic activity and/or binding capacity are used for the screening of agents. Similarly, NMDA-R mutants that maintain tyrosine phosphorylation activity and PTPL1-binding activity can be used. A functional derivative is prepared from a naturally occurring or recombinantly expressed PTPL1 and NMDA-R by proteolytic cleavage followed by conventional purification procedures known to those skilled in the art. Alternatively, the functional derivative is produced by recombinant DNA technology by expressing only fragments of PTPL1 or NMDA-R in suitable cells. In one embodiment, the partial receptor or phosphatase polypeptides are expressed as fusion polypeptides. It is well within the skill of the ordinary practitioner to prepare mutants of naturally occurring NMDA/PTPL1 proteins that retain the desired properties, and to screen the mutants for binding and/or enzymatic activity. Typically, functional derivatives of NMDA-R subunits NR2A and NR2B that bind PTPL1 will include the "tSXV motif" of these subunits. NR2A and NR2B derivatives that can be dephosphorylated typically comprise the cytoplasmic domain of the polypeptides, e.g., the C-terminal 900 amino acids or a fragment thereof. PTPL1 deletion constructs carrying only PDZ2+3 are able to bind the C-terminal 400 amino acids of NR2B in vitro. Functional derivatives of PTPL1 that bind the NMDA-R include the PDZ2 domain. Functional derivatives that retain enzymatic (dephosphorylation) activity include the C-terminal PTP domain.

In some embodiments, cells expressing PTPL1 and NMDA-R may be used as a source of PTPL1 and/or NMDA-R, crude or purified, or in a membrane preparation, for testing in these assays. Alternatively, whole live or fixed cells may be used directly in those assays. Methods for preparing fixed cells or membrane preparations are well known in the art, see, e.g., U.S. Pat. No. 4,996,194. The cells may be genetically engineered to coexpress PTPL1 and NMDA-R. The cells may also be used as host cells for the expression of other recombinant molecules with the purpose of bringing these molecules into contact with PTPL1 and/or NMDA-R within the cell.

IV. Therapeutic Applications and Pharmaceutical Compositions

It is well known in the art that NMDA-R agonists and antagonists can be used to treat symptoms caused by abnormal NMDA-R signaling (e.g., acute insult of the central nervous system (CNS)). Methods of treatment using pharmaceutical composition comprising NMDA agonists and/or NMDA antagonists have been described, e.g., in U.S. Pat. No. 5,902,815. As discussed in detail below, the present invention provides pharmaceutical compositions containing PTPL1 antagonists and/or agonists that modulate NMDA-R tyrosine phosphorylation. Such agonists and antagonists include, but are not limited to, agents that interfere with PTPL1 gene expression, agents that modulate the ability of PTPL1 to bind to NMDA-R or to dephosphorylate NMDA-R. In one embodiment, a PTPL1 antisense oligonucleotide is used as a PTPL1 antagonist in the pharmaceutical compositions of the present invention. In addition, PTP inhibitors that inhibit PTPL1 dephosphorylation of NMDA-R are useful as NMDA-R signaling modulators (e.g., orthovanadate, Li et al., Biochim. Biophys. Acta. 1405:110–20, 1998).

A. Therapeutic Application of the Present Invention

Abnormal NMDA-R activity elicited by endogenous glutamate is implicated in a number of important CNS disorders. In one aspect, the present invention provides modulators of PTPL1 that, by modulating phosphotyrosine level of NMDA-R, can treat or alleviate symptoms mediated by abnormal NMDA-R signaling.

One important use for NMDA antagonist drugs involves the ability to prevent or reduce excitotoxic damage to neurons. In some embodiments, the PTPL1 agonists of the present invention, which promote the dephosphorylation of NMDA-R, are used to alleviate the toxic effects of excessive NMDA-R signaling. In certain other embodiments, PTPL1 antagonists of the present invention, which function as NMDA-R agonists, are used therapeutically to treat conditions caused by NMDA-R hypo-function, i.e., abnormally low levels of NMDA-R signaling in CNS neurons. NMDA-R hypofunction can occur as an endogenous disease process. It can also occur as a drug-induced phenomenon, following administration of an NMDA antagonist drug. In some related embodiments, the present invention provides pharmaceutical compositions containing PTPL1 antagonists that are used in conjunction with NMDA antagonists, e.g., to prevent the toxic side effects of the NMDA antagonists.

B. Specific Examples of Diseases and Disorders to be Treated

Excessive glutamatergic signaling has been causatively linked to the excitotoxic cell death during an acute insult to the central nervous system such as ischemic stroke (Choi et al., Annu Rev Neurosci. 13: 171–182, 1990; Muir & Lees, Stroke 26: 503–513, 1995). Excessive glutamatergic signaling via NMDA receptors has been implicated in the profound consequences and impaired recovery after the head trauma or brain injury (Tecoma et al., Neuron 2:1541–1545, 1989; McIntosh et al., J. Neurochem. 55:1170–1179, 1990). NMDA receptor-mediated glutamatergic hyperactivity has also been linked to the process of slow degeneration of neurons in Parkinson's disease (Loopuijt & Schmidt, Amino Acids, 14: 17–23, 1998) and Huntington's disease (Chen et al., J. Neurochem. 72:1890–1898, 1999). Further, elevated NMDA-R signaling in different forms of epilepsy have been reported (Reid & Stewart, Seizure 6: 351–359, 1997).

Accordingly, PTPL1 agonists of the present invention are used for the treatment of these diseases or disorders by stimulating the NMDA receptor-associated phosphatase activity (such as that of PTPL1) or by promoting the binding of PTPL1 to the NMDA receptor complex.

The PTPL1 agonists (NMDA-R antagonists) of the present invention can also be used to treat diseases where a mechanism of slow excitotoxicity has been implicated (Bittigau & Ikonomidou, J. Child. Neurol. 12: 471–485, 1997). These diseases include, but are not limited to, spinocerebellar degeneration (e.g., spinocerebellar ataxia), motor neuron diseases (e.g., amyotrophic lateral sclerosis (ALS)), mitochondrial encephalomyopathies. The PTPL1 agonists of the present invention can also be used to alleviate neuropathic pain, or to treat chronic pain without causing tolerance or addiction (see, e.g., Davar et al., Brain Res. 553: 327–330, 1991).

On the other hand, NMDA-R hypofunction have been causatively linked to schizophrenic symptoms (Tamminga, Crit. Rev. Neurobiol. 12: 21–36, 1998; Carlsson et al., Br. J. Psychiatry Suppl.: 2–6, 1999; Corbett et al., Psychopharmacology (Berl). 120: 67–74, 1995; Mohn et al., Cell 98: 427–436, 1999) and various forms of cognitive deficiency, such as dementias (e.g., senile and HIV-dementia) and Alzheimer's disease (Lipton, Annu. Rev. Pharmacol. Toxicol. 38:159–177, 1998; Ingram et al., Ann. N.Y. Acad. Sci. 786: 348–361, 1996; Muller et al., Pharmacopsychiatry. 28: 113–124, 1995). In addition, NMDA-R hypofntction is also linked to psychosis and drug addiction (Javitt & Zukin, Am J Psychiatry. 148: 1301–8, 1991). Further, NMDA-R hypofunction is also associated with ethanol sensitivity (Wirkner et al., Neurochem. Int. 35: 153–162, 1999; Yagi, Biochem. Pharmacol. 57: 845–850, 1999).

Using PTPL1 antagonist (NMDA-R agonists) described herein, the present invention provides methods for the treatment of Schizophrenia, psychosis, cognitive deficiencies, drug addiction, and ethanol sensitivity by antagonizing the activity of the NMDA-R-associated PTPs, and that of PTPL1 in particular, or by inhibiting the interaction between PTPL1 and the NR2A or NR2B subunit.

C. Dosages and Modes of Administration

The PTPL1 agonists and antagonists of the present invention are directly administered under sterile conditions to the host to be treated. However, while it is possible for the active ingredient to be administered alone, it is often preferable to present it as a pharmaceutical formulation. Formulations typically comprise at least one active ingredient together with one or more acceptable carriers thereof. Each carrier should be both pharmaceutically and physiologically acceptable in the sense of being compatible with the other ingredients and not injurious to the patient. For example, the bioactive agent is complexed with carrier proteins such as ovalbumin or serum albumin prior to their administration in order to enhance stability or pharmacological properties such as half-life. Furthermore, therapeutic formulations of this invention are combined with or used in association with other therapeutic agents.

The therapeutic formulations are delivered by any effective means which could be used for treatment. Depending on the specific NMDA-R antagonist and/or NMDA-R agonist being used, the suitable means include but are not limited to oral, rectal, nasal, pulmonary administration, or parenteral (including subcutaneous, intramuscular, intravenous and intradermal) infusion into the bloodstream.

Therapeutic formulations are prepared by any methods well known in the art of pharmacy. See, e.g., Gilman et al (eds.) (1990) Goodman and Gilman's: The Pharmacological Bases of Therapeutics (8th ed.) Pergamon Press; and (1990) Remington's Pharmaceutical Sciences (17th ed.) Mack Publishing Co., Easton, Pa.; Avis et al (eds.) (1993) Pharmaceutical Dosage Forms: Parenteral Medications Dekker, N.Y.; Lieberman et al. (eds.) (1990) Pharmaceutical Dosage Forms: Tablets Dekker, N.Y.; and Lieberman et al (eds.) (1990) Pharmaceutical Dosage Forms: Disperse Systems Dekker, N.Y. The therapeutic formulations can conveniently be presented in unit dosage form and administered in a suitable therapeutic dose. The preferred dosage and mode of administration of a PTPL1 agonist and/or antagonist will vary for different patients, depending upon factors that will need to be individually reviewed by the treating physician. As a general rule, the quantity of a PTPL1 agonist and/or antagonist administered is the smallest dosage which effectively and reliably prevents or minimizes the conditions of the patients.

A suitable therapeutic dose is determined by any of the well known methods such as clinical studies on mammalian species to determine maximum tolerable dose and on normal human subjects to determine safe dosage. In human patients, since direct examination of brain tissue is not feasible, the appearance of hallucinations or other psychotomimetic symptoms, such as severe disorientation or incoherence, should be regarded as signals indicating that potentially neurotoxic damage is being generated in the CNS by an NMDA-R antagonist. Additionally, various types of imaging techniques (such as positron emission tomography and magnetic resonance spectroscopy, which use labeled substrates to identify areas of maximal activity in the brain) may also be useful for determining preferred dosages of NMDA-R agonists for use as described herein, with or without NMDA-R antagonists.

It is also desirable to test rodents or primates for cellular manifestations in the brain, such as vacuole formation, mitochondrial damage, heat shock protein expression, or other pathomorphological changes in neurons of the cingulate and retrosplenial cerebral cortices. These cellular changes can also be correlated with abnormal behavior in lab animals.

Except under certain circumstances when higher dosages may be required, the preferred dosage of a PTPL1 agonist and/or antagonist will usually lie within the range of from about 0.001 to about 1000 mg, more usually from about 0.01 to about 500 mg per day. It should be understood that the amount of any such agent actually administered will be determined by a physician, in the light of the relevant circumstances that apply to an individual patient (including the condition or conditions to be treated, the choice of composition to be administered, including the particular PTPL1 agonist or the particular PTPL1 antagonist, the age, weight, and response of the individual patient, the severity of the patient's symptoms, and the chosen route of administration). Therefore, the above dosage ranges are intended to provide general guidance and support for the teachings herein, but are not intended to limit the scope of the invention.

V. Methods for Purification of PTPL1

The present invention provides methods for purification of the PTPL1 protein or a polypeptide containing the PDZ2 domain of PTPL1. Specifically, identification of the binding between PTPL1 and NR2A or NR2B allows affinity purification of PTPL1 or polypeptide containing the PDZ2 domain of PTPL1, using methods well known in the art. For standard methods for affinity purification of proteins, see, e.g., *Protein Purification, Principles, High Resolution Methods and Applications*, Janson and Ryden eds., 1989; Scopes, R. K., Chapter 3, *Protein Purification, Principles and Practice*, 2nd Ed., Springer-Verlag, New York, 1987; Deutscher, M. P., *Guide to Protein Purification*, Academic Press, 1990, pp. 174–193.

In one embodiment, a polypeptide containing the PTPL1-binding site of NMDA-R is attached to a solid matrix (e.g., CNBr-activated Sepharose). The remaining active sites on the matrix are blocked with a suitable agent (e.g., BSA). After applying the biological preparation to the matrix and allowing binding of PTPL1 to the polypeptide containing the PTPL1-binding site of NMDA-R on the matrix, the matrix is washed to remove non-specific binding molecules from the matrix. PTPL1 or polypeptide containing the PDZ2 domain of PTPL1 can then be eluted from the matrix and recovered according to methods well known in the art.

VI. EXAMPLES

The following examples are provided to further illustrate the present invention. They are not included to limit the invention in any way.

Example 1

Identification of the NMDA-R/PTPL1 Binding Using Yeast Two-hybrid Screen

A yeast two-hybrid screen was carried out as follows. A commercially available human fetal brain cDNA library in the pACT2 vector pretransformed to the Y187 yeast strain (Clontech) was used. The cDNA corresponding to the 600 C-terminal amino acid residues of the NR2B subunit was fused with GAL4 BD by cloning it into the pAS2-1 vector (Clontech). The resulting GAL4BD-NR2B plasmid (bait) was transformed to Y190 strain (Clontech) to screen for the NR2B C-terminus interacting proteins in the human fetal brain cDNA library. Approximately $50 \times 10^6$ Y187 cells were mated in rich (YPD) medium for 20 hours with at least a ten-fold excess of Y190 cells carrying the bait vector. For selection of interactors, the yeast cells were plated for selection after mating on the solid yeast medium depleted of histidine and adenine. The AD plasmids from only those colonies which survived the double growth-selection and yielded strong colorimetric reaction in the β-galactosidase assay were further analyzed by DNA sequencing. Two yeast colonies contained identical cDNA clones which, in frame with the GAL4 AD, coded for the PDZ2 domain of protein tyrosine phosphatase PTPL1 together with some flanking sequence (127 amino acids N-terminally and 36 amino acids C-terminally). These results demonstrated that the PDZ2 domain of PTPL1 physically interacts with the NR2B subunit of NMDA-R.

The interaction between the C-terminus of NR2A and the PDZ2 domain of PTPL1 was demonstrated in an experiment where cDNA encoding the C-terminal 600 amino acids of NR2A was inserted into the GAL4 BD plasmid (pAS2-1). This plasmid, along with the GAL4 AD plasmid (pACT2) which contains the PDZ2 domain of PTPL1, was transformed to Y187 yeast cells. Growth on selective medium was observed. This indicates that NR2A, the second most tyrosine-phosphorylated NMDA-R subunit in the brain, interacts with PTPL1.

Example 2

"Pull-down" Experiments Demonstrating PTPL1/NMDA-R Interaction

"Pull-down" experiments demonstrating PTPL1/NMDA-R interaction are performed as follows. The portions of NR2A and NR2B containing the C-terminal 145 amino acids were expressed as fusion proteins with glutathione-S-transferase (GST) in *E. coli*. Bacterial cells from 25 ml LB medium harboring expressed proteins are lysed by sonication (10s) on ice, and bacterial debris pelleted by centrifuging the sonicate for 20 min at 15,000 g. Expressed proteins are purified by adding the supernatant to 100 μl of 50% Glutathione-Sepharose-4B (Pharmacia) bead slurry in phosphate buffered saline (PBS), incubated by shaking for 30 min at 4° C. Non-specifically bound proteins are removed by three washes of beads with ice-cold PBS. The purified GST-NR2A and GST-NR2B proteins attached to the beads are mixed with the PTPL1 protein tagged with the c-myc epitope and heterologously expressed in 293/COS cells, and washed to remove non-specifically bound proteins. The binding of PTPL1 to the C-termini of NR2A or NR2B is determined by Western blotting using anti-c-myc antibodies (Clontech).

For the negative control, the GST-NR2B fusion in which the valine residue in the very C-terminus is mutated to alanine is used. Furthermore, synthetic inhibitory peptides (KLSSIESDV) corresponding to the C-terminal nine amino acids of NR2A or NR2B are used for competition at a concentration of 0.5 mM to demonstrate the specificity of the interaction. For positive control, heterologously expressed post synaptic density 95 (PSD95, see, Niethammer et al., J. Neurosci. 16: 2157–63, 1996) is used in the similar set of experiments.

In the reverse experiment, the GST fusion with the second PDZ domain of PTPL1 is expressed in *E. Coli*, purified and used to bind both the heterologously expressed NR2A or NR2B as well as to capture NR2A or NR2B subunits from the rat brain lysate. The specific binding of NR2A or NR2B to GST-PTPL1 is detected by Western blotting using specific anti-NR2A or NR2B antibodies (Chemicon).

For positive control, synthetic inhibitory peptides corresponding to the C-terminal nine amino acids of NR2A or NR2B (KLSSIESDV) are used for competition at a concentration of 0.5 mM to demonstrate the specificity of the interaction.

Example 3

NMDA-R/PTPL1 Binding: Co-immunoprecipitation

Co-immunoprecipitation experiments demonstrating the NMDA-R/PTPL1 binding are performed as follows.

The combinations of eukaryotic CMV promoter driven expression vectors that contain cDNAs encoding the following proteins are co-expressed in 293/COS cells:

1. NR2A and c-myc tagged PTPL1
2. NR2B and c-myc tagged PTPL1
3. NR1, NR2A and c-myc tagged PTPL1
4. NR1, NR2B and c-myc tagged PTPL1
5. NR1, NR2A and GFP-[PDZ1+2 of PTPL1]

6. NR1, NR2B and GFP-[PDZ1+2 of PTPL1]

7. NR1, NR2A and GFP-[PDZ1+2 of PSD95] as a control

For all experiments, 5 micrograms of total plasmid DNA per semi-confluent dish of cells can be transfected by, e.g., calcium phosphate precipitation (Wigler M, et al., Cell 16:777–785, 1979). Cells can be harvested 48 hours post-transfection, the medium removed upon centrifugation and the cells resuspended in phosphate buffered saline (PBS) and lysed by Ultraturrax (IKA-Maschinenbau).

The following antibodies (usually at the concentration of 0.5–1 µg/ml) are added to the solution (0.5 ml total volume) in each case:

1. anti-NR2A or anti-c-myc
2. anti-NR2B or anti-c-myc
3. anti-NR1 or anti-c-myc
4. anti-NR1 or anti-c-myc
5. anti-NR1 or anti-GFP
6. anti-NR1 or anti-GFP
7. anti-NR1 or anti-GFP After co-incubation (at least 1 hour at 4° C.) of antibodies and heterologously expressed proteins, 20 µl of Protein A-Sepharose (Pharmacia) slurry is added, and the incubation is continued for another hour. To determine co-immunoprecipitated proteins, material bound to Protein A-Sepharose is separated by pelleting the beads with the immunocomplex attached by centrifugation, washed with PBS and resolved by 12% SDS-PAGE. Proteins resolved on the gel are transferred to membrane to verify the presence of co-immunoprecipitated proteins by Western blots using specific antibodies as outlined above.

To demonstrate the specificity of co-immunoprecipitation, the experiment is also carried out in the presence of synthetic inhibitory peptides (0.5 mM) corresponding to the C-terminal nine amino acids of NR2A or NR2B (KLSSIESDV) as well as control peptides corresponding to scrambled peptides with the same amino acid composition.

Example 4

Co-localization of PTPL1 and NMDA-R

Using an antisense oligonucleotide (5'-CCATCACCCGCACCACGAAG CCCTTCAGCTGCTG-CATTCTCA 3'), in situ hybridization studies were carried out to examine PTPL1 expression in rat brain. The results indicate that PTPL1 is expressed in all major neuronal populations in the adult rat brain. Thus, there is a very high degree of overlap between the cellular localization of PTPL1 and NMDA-R in the brain.

In primary neuronal culture derived from the rat cerebral cortex and hippocampus, the studies of co-localization were conducted with the recombinantly expressed PTPL1. In such an experiment, a plasmid carrying cDNA construct (5 micrograms of DNA) encoding GFP-PTPL1 fusion protein was transfected to primary neurons using lipofection. The clustering of the GFP-PTPL1 fusion was observed in dendritic processes, which serve as input receivers from other cells and where NMDA-R are localized. The co-localization of GFP-PTPL1 and NMDA-R can be demonstrated by immunocytochemistry using anti-NMDA-R antibodies.

High resolution immunohistochemistry studies on brain slices (50–200 micrometers in thickness) are carried out to demonstrate the subcellular co-localization as described in Antibodies, Harlow & Lane, Eds., 1999. Using NR1- and PTPL1-specific antibodies to label endogenous NMDA-R and PTPL1 in neurons, the co-localization is detected by using antibodies derived from different species (such as rabbit or mouse; rabbit or goat etc.). The secondary antibodies which carry different reporters (e.g., different fluorescent tags) and specifically recognize antibodies from a particular species are used to differentiate between NMDA-R and PTPL1.

Example 5

Dephosphorylation of NR2A or NR2B by PTPL1

To demonstrate that PTPL1 can dephosphorylate NR2A or NR2B and that the efficacy of dephosphorylation is dependent on the interaction between the C-terminus of either NR2A or NR2B and the PDZ2 domain of PTPL1, the following experiments are conducted.

The purified GST-NR2A and GST-NR2B proteins are phosphorylated in vitro by purified Src or Fyn kinases (1 unit, Upstate Biotechnology in 50 µl HEPES, 20 mM, pH 7.2) at 30° C. for 10 min in the presence of $Mg^{2+}$-ATP (1 mM). Purified GST protein is used as a control to assess the NR2A- or NR2B-specific tyrosine phosphorylation. Upon tyrosine phosphorylation, the proteins are resolved by SDS-PAGE (12%), blotted and probed with anti-phosphotyrosine antibodies linked to the horseradish peroxidase reporter system (Upstate Biotechnology). The levels of tyrosine phosphorylation are determined from the intensity of the phosphotyrosine signal.

Simultaneously, the recombinant c-myc tagged PTPL1 is expressed in the heterologous system such as HEK293 or COS cells. 5 µg of total plasmid DNA per semi-confluent dish (100 mm diameter) of cells is transfected by, e.g., calcium phosphate precipitation. Cells are harvested 48 hours post-transfection, the medium removed upon centrifugation and the cells resuspended in phosphate buffered saline (PBS) and lysed by Ultraturrax (IKA-Maschinenbau). Nuclei are pelleted by centrifugation at 1000 g for 10 min.

The c-myc antibodies (at the concentration of 0.5–1 µg/ml) are added to the supernatant (0.5 ml total volume). After co-incubation (at least 1 hour at 4° C.) of antibodies and heterologously expressed proteins, 20 µl of Protein A-Sepharose (Pharmacia) slurry is added, and the incubation is continued for another hour.

The captured protein A-PTPL1 immunocomplex is used to study the rate of dephosphorylation of the kinase-treated fusion proteins: GST-NR2A, GST-NR2B and GST-NR2B with the C-terminal Val to Ala mutation. This is done by adding the immunoprecipitated PTPL1 immuno-complex to the phosphorylated GST-NR2A or GST-NR2B proteins in 100 µl dephosphorylation buffer (25 mM imidazole, pH 7.2 with HCl, bovine serum albumin at 1 mg/ml, 1 mM DTT). Aliquots are taken every 5 minutes, the fusion proteins are resolved by SDS-PAGE (12%), blotted to nitrocellulose membrane (Amersham Pharmacia Biotech) and levels of dephosphorylation of the C-termini of NR2A or NR2B assessed using anti-phosphotyrosine antibodies (Upstate Biotechnology).

The control experiments are conducted in the presence of 0.5 mM synthetic inhibitory peptides corresponding to the C-terminal nine amino acids of NR2A or NR2B (KLSSIESDV) as well as control peptides corresponding to scrambled peptides with the same amino acid composition.

Example 6

Modulation of NMDA-R Signaling by PTPL1: Electrophysiology Analysis

The following experiments are conducted to determine the role of PTPL1 in the modulation of NMDA-R signaling.

In the recombinant system, 293 cells are transfected with plasmids encoding NR1, NR2A or NR2B subunits of NMDA-R with or without PTPL1. 5 micrograms of total plasmid DNA per semi-confluent dish of cells is transfected by, e.g., calcium phosphate precipitation (Wigler M et al., Cell. 1979, 16:777–785). The cells co-expressing all components respond with the NMDA-R selective current when exposed to L-glutamate or NMDA. In order to measure NMDA currents, the cells are clamped with the patch pipette and characteristic NMDA-R currents recorded at different membrane potentials (Kohr & Seeburg, J. Physiol (London) 492: 445–452, 1996). Purified Src or Fyn are then allowed to diffuse to the cytosol of clamped cells through the patch pipette. Once again, the NMDA currents are recorded and the potentiation by the tyrosine kinases of NMDA-R currents is determined both in the presence and absence of transfected PTPL1.

Alternatively, instead of applying purified Src or Fyn, a peptide, EPQ(pY)EEIPIA, that activates the members of Src family of tyrosine kinases is used to activate endogenous kinases in the cell and the NMDA-R currents are determined both in the presence and absence of transfected PTPL1.

Patch clamp experiments with cells expressing NMDA-R and PTPL1 are carried out in the presence of 0.5 mM synthetic inhibitory peptides corresponding to the C-terminal nine amino acids of NR2A or NR2B (KLSSIESDV), as well as control peptides corresponding to the scrambled peptides with the same amino acid composition as the inhibitory peptide.

Example 7

Screening for Agents which Modulate NMDA-R Signaling

One approach to screen for agents which modulate NMDA-R signaling is described as follows.

The C-terminal portions of NR2A or NR2B are expressed as fusion proteins with glutathione-S-transferase (GST) in *E. coli*, purified using Glutathione-Sepharose-4B beads (Pharmacia). The purified GST-NR2A or GST-NR2B proteins on beads are mixed with purified Src or Fyn kinases (e.g. from Upstate Biotechnology) in the presence of 1 mM $Mg^{2+}$-ATP.

Equal amounts of phosphorylated pure GST-NR2A or NR2B on the beads are aliquoted to 96- or 384-well assay plate containing PTPL1 or its enzymatically active derivatives thereof in the absence or presence of the agents, one pool of agents or one agent per well. The control wells contain no PTPL1. After incubation, equal amounts of phosphotyrosine antibodies in binding buffer (phosphate buffered saline) are added to each well.

Phosphotyrosine antibodies themselves can embody fluorescent markers such as fluorescein or rhodamine. Alternatively, secondary antibodies that are coupled to fluorescent markers and recognize the phosphotyrosine antibodies are added at this stage.

The rate of disappearance of fluorescence as compared to control (no agents added) is indicative of the impact of the agents on the PTPL1 activity. Agents which slow down the removal of phosphate groups are PTPL1 antagonists. In contrast, agents facilitating the removal of phosphate groups are PTPL1 agonists.

Similarly, radioactive $\gamma$-[$^{32}$P]ATP can be used to phosphorylate purified GST-NR2A or GST-NR2B proteins on beads using purified Src or Fyn kinases (e.g., obtainable from Upstate Biotechnology). Equal amounts of phosphorylated pure GST-NR2A or NR2B on the beads are aliquoted to 96- or 384-well assay plate containing PTPL1 or its enzymatically active derivatives thereof in the absence or presence of the agents, one pool of agents or one agent per well. The control wells contain no PTPL1. After incubation, equal aliquots are removed and radioactivity retained on beads counted.

The rate of disappearance of radioactivity as compared to control (no agents added) is indicative of the impact of the agents on the PTPL1 activity. Agents which slow down the removal of phosphate groups are PTPL1 antagonists. In contrast, agents facilitating the removal of phosphate groups are PTPL1 agonists.

Many modifications and variations of this invention can be made without departing from its spirit and scope, as will be apparent to those skilled in the art. The specific embodiments described herein are for illustration only and are not intended to limit the invention in any way.

All publications, figures, patents and patent applications cited herein are hereby expressly incorporated by reference for all purposes to the same extent as if each was so individually denoted.

What is claimed is:

1. A method for identifying a modulator of N-methyl-D-aspartate receptor (NMDA-R) signaling activity, comprising detecting the ability of an agent to modulate the phosphatase activity of a protein tyrosine phosphatase L1 (PTPL1) on a NMDA-R or to modulate the binding of the PTPL1 to NMDA-R, thereby identifying the modulator, wherein the PTPL1 is capable of dephosphorylating NMDA-R.

2. The method of claim 1, wherein the PTPL1 is human.

3. The method of claim 2, wherein the modulator is identified by detecting its ability to modulate the phosphatase activity of the PTPL1.

4. The method of claim 1, wherein the modulator is identified by detecting its ability to modulate the binding of the PTP to the NMDA-R.

5. A method for identifying an agent as a modulator of NMDA-R signaling, comprising:
   (a) contacting
      (i) the agent
      (ii) PTPL1; and
      (iii) NMDA-R or a subunit thereof;
   wherein either (ii) and (iii), or both (ii) and (iii), is substantially pure or recombinantly expressed;
   (b) measuring the tyrosine phosphorylation level of the NMDA-R or subunit;
   (c) comparing the NMDA-R tyrosine phosphorylation level in the presence of the agent with the NMDA-R tyrosine phosphorylation level in the absence of the agent,
   wherein a difference in tyrosine phosphorylation levels identifies the agent as a modulator of NMDA-R signaling.

6. The method of claim 5, wherein the NMDA-R and the PTPL1 exist in a PTPL1/NMDA-R-containing protein complex.

7. The method of claim 5, wherein the agent enhances the ability of the PTPL1 to dephosphorylate the NMDA-R.

8. The method of claim 5, wherein the agent inhibits the ability of the PTPL1 to dephosphorylate the NMDA-R.

9. The method of claim 5, wherein the agent modulates binding of the PTPL1 to the NMDA-R.

10. The method of claim 9, wherein the agent promotes or enhances the binding.

11. The method of claim 9, wherein the agent disrupts or inhibits the binding.

12. A method for identifying a nucleic acid molecule which encodes a gene product that modulates NMDA-R signaling, comprising:

(a) obtaining a cell culture coexpressing the NMDA-R and PTPL1

(b) introducing a nucleic acid molecule encoding a gene product into a portion of the cells; thereby producing cells comprising the nucleic acid molecule;

(c) culturing the cells in (b) under conditions in which the gene product is expressed;

(d) measuring the tyrosine phosphorylation level of the NMDA-R in the cells in (c) and comparing the level with that of control cells into which the nucleic acid molecule has not been introduced wherein a difference in tyrosine phosphorylation levels identifies the nucleic acid molecule as a modulator of NMDA-R signaling.

* * * * *